United States Patent [19]

Flahive

[11] Patent Number: 5,965,487
[45] Date of Patent: Oct. 12, 1999

[54] MIXED HERBICIDAL COMPOSITIONS

[75] Inventor: Eamon Flahive, Oxon, United Kingdom

[73] Assignee: Dow AgroSciences LLC, Indianapolis, Ind.

[21] Appl. No.: 08/913,333

[22] PCT Filed: Mar. 8, 1996

[86] PCT No.: PCT/US96/03289

§ 371 Date: Sep. 12, 1997

§ 102(e) Date: Sep. 12, 1997

[87] PCT Pub. No.: WO96/28027

PCT Pub. Date: Sep. 19, 1996

[30] Foreign Application Priority Data

Mar. 15, 1995 [GB] United Kingdom .................... 9505204

[51] Int. Cl.$^6$ ............................ A01N 43/40; A01N 37/10
[52] U.S. Cl. ......................... 504/130; 504/142; 504/144; 504/145; 504/146; 71/DIG. 1
[58] Field of Search ...................... 504/130, 142, 504/145, 146, 144; 71/DIG. 1

[56] References Cited

U.S. PATENT DOCUMENTS

| | | | |
|---|---|---|---|
| 4,637,830 | 1/1987 | Dyer et al. ........................... | 71/DIG. 1 |
| 5,152,823 | 10/1992 | Albrecht et al. ..................... | 71/DIG. 1 |
| 5,374,603 | 12/1994 | Mulqueen et al. ..................... | 504/130 |
| 5,834,006 | 11/1998 | Smith et al. ........................... | 424/409 |

FOREIGN PATENT DOCUMENTS

| | | |
|---|---|---|
| 12044/88 | 2/1988 | Australia . |
| 60-276917 | 11/1985 | Japan . |

*Primary Examiner*—John Pak

[57] ABSTRACT

Homogeneous herbicidal compositions were prepared by dissolving a water-insoluble ester of fluroxypyr or triclopyr in an aqueous solution of an alkali metal or amine salt of an herbicidal acid, such as 2,4-D, MCPA, or dicamba.

13 Claims, No Drawings

MIXED HERBICIDAL COMPOSITIONS

This application is a 371 of PCT/US96/03289, filed on Mar. 8, 1996.

This invention relates to the field of agricultural chemicals, and in particular to the formulation of compositions of agricultural chemicals in forms convenient for application, by conventional spray techniques. Many agricultural chemicals, particularly herbicides, are water-insoluble, and their formulation into compositions which can be applied conveniently in the field therefore generally involves the use of various adjuvants and carriers, including, in particular, organic solvents. Organic solvents are, however, increasingly thought to be environmentally unacceptable, and much effort has been applied in recent years to the production of agricultural formulations which contain no organic solvents, or at least which have only low levels of organic solvents Attempts have also been made in recent years to co-formulate two or more herbicidally active compounds, in order to provide compositions with a broader spread of activity that can be achieved by use of one compound alone.

U.S. Pat. No. 4,637,830 is concerned with a herbicidal concentrate which addresses some of these needs, and provides a concentrate comprising a salt of a phenoxy acid herbicide, together with an alkanoate (particularly the octanoate) of ioxynil or bromoxynil. It is clear, however, from the disclosure of this reference that it is considered to be very surprising that the particular ioxynil and bromoxynil esters are compatible with the phenoxy acid salts, and indeed it is found that most herbicidal esters are not compatible with phenoxy acid salts in such a manner.

Detailed investigations subsequent to the date of U.S. Pat. No. 4,637,830 have indicated that the commonly established esters of herbicides such as fluroxypyr, and haloxyfop are not compatible with herbicidal acid salts, in that it is not possible to formulate the two herbicides together in a single phase aqueous composition.

WO-94/24866 is concerned with the preparation of herbicidal compositions which are emulsifiable concentrates, concentrated aqueous emulsions, wettable powders, or dispersable granules containing fluroxypyr derivatives. The fluroxypyr is present in the form of an ester which is a liquid at 25° C. Various other herbicides may also be present, in order to produce combination products, and phenoxy acids and their esters are mentioned. There is no mention however of salts of herbicidal acids, nor any suggestion that it might be possible to provide combination products of fluroxypyr esters which are aqueous solutions, rather than emulsions or emulsifiable (i.e., non-aqueous) concentrates.

We have now determined that a number of other herbicidal esters which are not structurally similar to ioxynil and bromoxynil alkanoates will dissolve in salts of acid herbicides, in particular salts of phenoxy acid herbicides, to provide storage stable single phase compositions. The esters in question surprisingly have in common the feature that they are liquids rather than solids, at 25° C. Because the herbicidal esters in question are not structurally similar to ioxynil and bromoxynil octanoate, it would not have been predicted from U.S. Pat. No. 4,637,830 that the use of these particular herbicidal esters would result in stable aqueous compositions.

Accordingly, in a first aspect of the invention, there is provided a herbicidal composition, which is a stable, homogeneous aqueous concentrate comprising a herbicidal salt, and a water-insoluble herbicide, wherein the herbicidal salt is a sodium, potassium, ammonia, dimethylamine, diethylamine, triethylamine, monoethanolamine, diethanolamine, or triethanolamine salt of 3,6-dichloro-2-methoxybenzoic acid (dicamba);
2,4-dichlorophenoxy acetic acid (2,4-D);
2-methyl-4-chlorophenoxy acetic acid (MCPA)
2-(2-methyl-4-chlorophenoxy) propionic acid (CMPP, mecoprop);
2-(2,4-dichlorophenoxy)propionic acid (2,4-DP);
4-(2-methyl-4-chlorophenoxy) butyric acid (MCPB);
4-(2,4-dichlorophenoxy)butyric acid (2,4-DB), or ((3,5,6-trichloro-2-pyridinyl)oxy)acetic acid (triclopyr)

and wherein the water-insoluble herbicide is an ester of fluroxypyr or triclopyr, which is a liquid at 25° C.

The herbicidal salt used in the concentrate of the present invention may have as its anion any of 3,6-dicloro-2-methoxybenzoic acid (dicamba);
2,4-di chloro-phenoxyacetic acid (2,4-D);
2-methyl-4-chlorophenoxy acetic acid (MCPA)
2-(2-methyl-4-chlorophenoxy) propionic acid (CMPP, mecoprop);
2-(2,4-dichlorophenoxy)propionic acid (2,4-DP);
4-(2-methyl-4-chlorophenoxy) butyric acid (MCPB);
4-(2,4-dichlorophenoxy)butyric acid (2,4-DB), or ((3,5,6-trichloro-2-pyridinyl)oxy)acetic acid (triclopyr)

The most preferred are 2,4-D, MCPA, and triclopyr.

The counter-ion may be sodium, potassium, ammonia, dimethylamine, diethylamine, monoethanolamine, triethylamine, diethanolamine, or triethanolamine, the dimethylamine, triethylamine, ethanolamine, and potassium salts being preferred.

The quantity of the herbicidal salt employed affects the solubility of the ester in the composition. Generally, the more herbicidal salt is employed, the greater the solubility of the ester. The amount of salt may be from 1 to 99 percent, preferably from 15 to 80 percent, more preferably from 40 to 70 percent by weight of the composition.

The water-insoluble herbicide employed in the present invention is an ester of fluroxypyr or triclopyr, which is is a liquid at 25° C. The ester is preferably formed with a $C_6$–$C_{12}$ alkanol, or a $C_6$–$C_{12}$ alkoxyalkanol. Liquid esters of fluroxypyr, in particular liquid esters of fluroxypyr with $C_6$–$C_{12}$ alkanols or $C_6$–$C_{12}$ alkoxyalkanols are particularly preferred. Especially preferred are the 1-butoxy-2-propyl, 1-butoxy-2-butyl, 1-(1-methoxy-2-propoxy)-2-propyl, 1-(1-butoxy-2-propoxy)-2-propyl, 1-(1-(1-methoxy-2-propoxy)-2-propoxy)-2-propyl, 1-(1-(1-butoxy-2-propoxy)-2-propoxy)-2-propyl, and 2-ethylhexyl esters, as discussed in WO-94/24866.

The esters of fluroxypyr of this invention can be prepared readily by methods well-known in the art, including the method described in EP-A-441457, which involves the preparation of the methyl or ethyl ester by alkylation of a salt of 4-amino-3,5-dichloro-6-fluoro-2-pyridinol with methyl or ethyl chloroacetate and subsequent transesterification with the desired alcohol.

The concentrate formulations of the present invention preferably contain from 1 to 50 percent by weight of the liquid ester, more preferably from 2.5 to 40 percent, most preferably from 5 to 30 percent. The weight ratio of the water-insoluble liquid ester to the herbicidal salt is preferably from 1:12 to 1:1, more preferably from 1:10 to 1:5, most preferably about 1:8.

The herbicidal salt component of the compositions may be a mixture of two or more herbicidal salts. Similarly, two or more water-insoluble liquid herbicidal esters may be used. When more than one herbicidal salt or more than one herbicidal ester is employed, the total amount of the salt or water-insoluble ester employed is preferably as indicated above.

A co-solvent may be employed to improve the dilution properties of the active materials. Suitable co-solvents are water-miscible materials, for example propyleneglycol ethers, propylenediethers, and pyrrolidones. Water immiscible solvents may also be used, particularly in conjunction with a water-miscible solvent (in particular, in conjunction with glycol solvents), in order to improve the solubility of the less soluble esters, particularly at low temperatures. Suitable water-immiscible solvents are those disclosed in WO-A-94/24866. The co-solvent may be present in an amount of from 1 to 20% by weight of the composition.

One or more surfactants may also be employed to improve the dilution properties. Any agriculturally acceptable surface active agent or combination of surface active agents can be employed. Examples of surface active agents that can be employed for one or more of the liquid esters of the invention include salts of alkylarylsulfonic acids (such as calcium dodecylbenzenesulfonate), alkylphenol-alkylene oxide addition products (such as nonylphenol-$C_{18}$-ethoxylate), alcohol-alkylene oxide addition products (such as tridecyl alcohol-$C_{16}$-ethoxylate) dialkyl esters of sulfosuccinic acid (such as sodium di-2-ethylhexyl sulfosuccinate), sorbitol esters (such as sorbitol oleate), polyalkylene esters of fatty acids (such as polyethylene glycol stearate), block copolymers of ethylene oxide and propylene oxide and salts of mono and dialkyl phosphate esters (such as potassium di-2-ethylhexyl phosphate). Some specific examples include alkali metal dialkyl sulfosuccinates sold under the name Anonaid™ or Empimin™, and fatty alcohol ethoxylates sold under the name Atlox™. Blends of ionic and non-ionic surfactants are generally preferred. Some specific examples include blends of calcium dodecylbenzene-sulfonate and block copolymers of ethylene oxide and propylene oxide sold under many names, including Atlox™ and Tensiofix™. An agriculturally acceptable surface active agent is a surface active agent that meets the requirements for use in agricultural products in at least one country. Particularly preferred are a nonyphenyl EO/PO block copolymer (MAKON NI-10™) and a $C_{13}$–$C_{15}$ alcohol ethoxylate (Synperonic A2™).

Surface active agents are typically present in concentrations of 1 to 20 percent, more preferably from 5 to 20 percent.

The formulations of the present invention may, optionally, contain other agriculturally acceptable adjuvants commonly used in formulated agricultural products, such as antifoam agents, compatibilizing agents, sequestering agents, neutralizing agents and buffers, corrosion inhibitors, dyes, odorants, penetration aids, spreading agents, dispersing agents, thickening agents, freeze point depressants, antimicrobial agents, crop oil, and the like.

The aqueous formulations may also contain a freeze-point depressant, such as propylene glycol, ethanol, propanol, ethylene glycol, glycerol, urea, and ammonium chloride. Propylene glycol is often preferred. Any agriculturally acceptable freeze-point depressant that does not destabilize or detract from the efficacy of the product, however, can be employed.

The aqueous compositions in accordance with the invention may be employed to produce dried herbicidal products, for example by spray-drying. Such spray-dried products may be prepared for application by simple dissolution in water. Compositions comprising the potassium salt of the herbicidal acid are particularly suitable for spray-drying.

Accordingly, the invention includes within its scope a dry herbicidal formulation obtained by spray drying a composition as referred to above.

Sprayable compositions in accordance with the invention may be prepared by diluting in water a concentrate in accordance with the invention, or by dissolving in water a spray dried composition in accordance with the invention.

The invention also includes within its scope a method of controlling or preventing the growth of weeds, which method comprises a composition according to the invention applying to the locus of the weeds.

A number of preferred embodiments of the invention are described in more detail in the following Examples.

General Method of Preparation

Two component herbicidal compositions comprising water-insoluble herbicide esters and herbicidal salts were prepared by simple mixing until a homogeneous liquid was obtained. The process may be accelerated by elevated temperatures of up to 60° C.

The herbicidal esters used in the Examples and comparative Examples have the following melting points:

|  | M. Pt. |
|---|---|
| fluroxypyr butoxypropyl ester | <25° C. |
| triclopyr butoxyethyl ester | <25° C. |
| fluroxypyr 1-butoxy-2-butyl ester | <25° C. |
| fluroxypyr 1-methoxy-2-propoxy-2-propyl ester | <25° C. |
| fluroxypyr 1-methoxy-2-propoxy-2-propoxy-2-propyl ester | <25° C. |
| haloxyfop ethoxyethyl ester (racemic) | 57° C. |
| fluroxypyr 1-methyl heptyl ester | 58° C. |
| fluroxypyr methyl ester | 125° C. |
| 2,(4-cyano-2-flurophenoxy) phenoxypriopianate | 45° C. |
| haloxyfop methyl ester (R-isomer) | 25° C. |

The following compositions were prepared.

EXAMPLES

In the following Examples, "wet basis" indicates the amounts of the various ingredients on the basis of the various commercial preparations (including water) used to prepare them. "Dry basis" indicates the equivalent dry weight of the same components. The term DMA indicates the dimethylamine salt.

|  | wet basis | dry basis |
|---|---|---|
| Example 1 | | |
| fluroxypyr butoxypropyl ester | 116 g/L | 116 g/L |
| 2,4-D concentrate (Commercial name DMA-6) | 810 g/L | 542 g/L |
| Water | to 1 L | 506 g/L |
| Example 2 | | |
| fluroxypyr butoxypropyl ester | 116 g/L | 116 g/L |
| 2,4-D concentrate (Commercial name DMA-6) | 810 g/L | 542 g/L |
| glycol ether (Dowanol PnB) | 116 | 116 g/L |
| Water | to 1 L | 390 g/L |
| Example 3 | | |
| fluroxypyr butoxypropyl ester | 116 g/L | 116 g/L |
| 2,4-D concentrate (Commercial name DMA-6) | 810 g/L | 542 g/L |

-continued

|  | wet basis | dry basis |
|---|---|---|
| Dowanol PnB | 116 g/L | 116 g/L |
| Surfactant MAKON NI-10 | 35 g/L | 35 g/L |
| Surfactant Synperonic A2 | 35 g/L | 35 g/L |
| Water | to 1 L | 320 g/L |
| Example 4 | | |
| fluroxypyr butoxypropyl ester | 134 g/L | |
| MCPA dimethylamine salt concentrate (Commercial name MCPA 750D) | 768 g/L | 514 g/L |
| Water | Balance to 1 L | |
| Example 5 | | |
| triclopyr butoxyethyl ester | 100 g/L | |
| 2,4-D concentrate (Commercial name DMA-6) | 900 g/L | 602 g/L |
| Example 6 | | |
| fluroxpyr 2-ethylhexyl | 100 g/L | |
| 2,4-D concentrate (Commercial name DMA-6) | 900 g/L | 602 g/L |
| Example 7 | | |
| fluroxypyr butoxypropyl ester | 100 g/L | |
| triclopyr trimethylamine salt (commercial formulation - Garlon 3A) | 900 g/L | 400 g/L |
| Example 8 | | |
| fluroxypyr tripropylene glycol monomethyl ether | 130 g/L | |
| 2,4-D concentrate (Commercial name DMA-6) | 870 g/L | 528 g/L |
| Example 9 | | |
| triclopyr butoxyethyl ester | 25 g/L | |
| triclopyr trimethylamine salt (commercial formulation - Garlon 3A) | 975 g/L | 433 g/L |
| Example 10 | | |
| fluroxypyr butoxypropyl ester | 100 g/L | |
| Mecoprop 640 D (DMA salt) | 900 g/L | 477 g/L |
| Example 11 | | |
| fluroxypyr butoxypropyl ester | 100 g/L | |
| MCPA 400K (potassium salt) | 975 g/L | 328 g/L |
| Example 12 | | |
| fluroxypyr dipropylene glycol monomethyl ether (DMA salt - Commercial name DMA-6) | 110 g/L | |
| 2,4-D concentrate | 890 g/L | 600 g/L |
| Example 13 | | |
| fluroxypyr 1-butoxy-2-butyl ester (DMA salt - Commercial name DMA-6) | 100 g/L | |
| 2,4-D concentrate | 900 g/L | 600 g/L |

All of the Examples produced clear homogeneous concentrates, which were stable at least on overnight storage.

Examples 1,2,3 and 4 were subjected to an accelerated ageing test, at a range of temperatures from −10° C. to 54° C., and were stable for up to 12 months.

Example 14

The composition of Example 11 was spray-dried to produce a fine powder. The powder could be readily redissolved in water to reconstitute the composition.

The composition of Example 3 was applied by spray to number of weed species in greenhouse trials.

The test species used in the test were:
 a. 2,4-D susceptible weeds (not controlled by fluroxypyr). *Papaver rhoeas* (field poppy) and *Chenopodium album* (fathen)
 b. Fluroxypyr susceptible weeds (not controlled by 2,4-D). *Galium aparine* (cleavers).
 c. Resistant to both components. *Anthemis cotula* (stinking mayweed).
 d. Crops: Wheat cv avalon Barley cv Igri Plants were grown under greenhouse conditions with both cultivation and test temperatures of min. 12° C., max. 20° C. Seeds were initially sown in trays of a peat compost and transplanted (at cotyledon to one leaf growth stage), into 7×7×8 cm pots of the same peat compost. There was one plant per pot and 5 replicate pots per treatment, at treatment growth stages were:

| *Galium aparine* | 2 whorls |
|---|---|
| *Anthemis cotula* | 7–8 leaves |
| *Papaver rhoeas* | 6–8 leaves |
| *Chenopodium album* | 4 leaves |
| Wheat and Barley | 1–1½ leaves |

The formulation of Example 3 was made up to the required doses using tap water, and applied by spray using an application volume of 200 l/ha.

Following treatment and after all foliage had dried, all plants were randomised in the greenhouse. Pots were watered by sub-pot irrigation.

Plants were assessed by visual comparison of treated plants with untreated plants. Difference was expressed as Mean Visual % Control. Plants were also harvested by cutting at ground level and weighing the foliage. Results were expressed as mean fresh weight in grams or as mean % reduction in fresh weight. Crops were assessed by measuring crop height in cm.

Results were subjected to statistical evaluation by multiple range analysis.

The combined formulation was at least as effective as the application of the two components separately.

Comparative Examples

Various other formulations were prepared using other herbicidal esters.

|  | wet basis | dry basis |
|---|---|---|
| Comparative Example 1 | | |
| haloxyfop ethoxyethylester (racemic) | 100 g/L | |
| 2,4-D DMA | 900 g/L | 602 g/L |
| Comparative Example 2 | | |
| fluroxypyr - 1 methyl heptyl ester | 100 g/L | |
| 2,4-D DMA | 900 g/L | 602 g/L |
| Comparative Example 3 | | |
| fluroxypyr methyl ester | 80 g/L | |
| 2,4-D DMA | 920 g/L | 615 g/L |
| Comparative Example 4 | | |
| 2,(4-cyano-2-flurophenoxy) phenoxypriopianate | 100 g/L | |
| 2,4-D DMA | 900 g/L | 602 g/L |
| Comparative Example 5 | | |
| haloxyfop methyl ester | 25 g/L | |
| 2,4-D DMA | 975 g/L | |

Although some of the compositions of Comparative Examples 1 to 5 could be formulated to produce clear solutions, by heating to 60° C., none was stable on overnight storage. Typically, the compositions would crystallise, sediment, or phase separate at ambient temperature.

The composition of the present invention are particularly suitable for the treatment of broadleaf weeds for example *Brassica species, Kochia species, Boreava species, Cirsium species*, Matricaria, Salsola (Russian thistle), Stellaria (chickweed) and Polygonum, in various crops, in particular in cereal crops, for example spring and winter wheat,spring and winter barley, and rye.

The formulations of the present invention reduce the amount of or eliminate organic solvents that are environmentally undesirable.

I claim:

1. A herbicidal composition which is a stable, homogeneous aqueous solution concentrate comprising a herbicidal salt and a dissolved water-insoluble herbicide wherein the herbicidal salt is about 15 to about 80 percent by weight of the composition and is a sodium, potassium, ammonia, dimethylamine, diethylamine, triethylamine, monoethanolamine, diethanolamine, or triethanolamine salt of 3,6-dichloro-2-methoxybenzoic acid (dicamba); 2,4-dichlorophenoxyacetic acid (2,4-D); 2-methyl-4-chlorophenoxyacetic acid (MCPA); 2-(2-methyl-4-chlorophenoxy) propionic acid (CMPP, mecoprop); 2-(2,4-dichlorophenoxy) propionic acid (2,4-DP); 4-(2-methyl-4-chlorophenoxy) butyric acid (MCPB); 4-(2,4-dichlorophenoxy)butyric acid (2,4-DB); or ((3,5,6-trichloro-2-pyridinyl)oxy)acetic acid (triclopyr) and the water-insoluble herbicide is about 2.5 to about 40 percent by weight of the composition and is a $C_6$–$C_{12}$ alkanol or $C_6$–$C_{12}$ alkoxyalkanol ester of fluroxypyr or triclopyr or 1-(1-(1-butoxy-2-propoxy)-2-propoxy)-2-propyl ester of fluroxypyr which is a liquid at 25° C. and wherein the weight ratio of water-insoluble herbicide to herbicidal salt is about 1:12 to about 1:1; and wherein the composition contains essentially no water-miscible or water-immiscible co-solvent.

2. A composition as claimed in claim 1 wherein the water-insoluble herbicide is said ester of fluroxypyr.

3. A composition as claimed in claim 2, wherein the water-insoluble herbicide is a 1-butoxy-2-propyl, 1-butoxy-2-butyl, 1-(1-methoxy-2-propoxy)-2-propyl, 1-(1-butoxy-2-propoxy)-2-propyl, 1-(1-(1-methoxy-2-propoxy)-2-propoxy)-2-propyl, 1-(1-(1-butoxy-2-propoxy)-2-propoxy)-2-propyl, or 2-ethylhexyl ester.

4. A composition as claimed in claim 1 wherein the herbicidal salt is said salt of 2,4-D or MCPA.

5. A composition as claimed in claim 4 wherein the herbicidal salt is the dimethylamine, triethylamine, potassium, or ethanolamine salt.

6. A composition as claimed in claim 1, wherein the amount of the herbicidal salt is from 40 to 70 percent by weight of the composition.

7. A composition as claimed in claim 1, wherein the amount of the water-insoluble herbicide is from 5 to 30 percent by weight of the composition.

8. A sprayable herbicidal composition prepared by diluting a composition as claimed in claim 1 with water.

9. A method of controlling the growth of weeds, which method comprises applying to the locus of the weeds a composition as claimed in claim 8.

10. A composition as claimed in claim 8 wherein the water-insoluble herbicide is a 1-butoxy-2-propyl, 1-butoxy-2-butyl, 1-(1-methoxy-2-propoxy)-2-propyl, 1-(1-butoxy-2-propoxy)-2-propyl, 1-(1-(1-methoxy-2-propoxy)-2-propoxy)-2-propyl, 1-(1-(1-butoxy-2-propoxy)-2-propoxy)-2-propyl, or 2-ethylhexyl ester of fluroxypyr.

11. A composition as claimed in claim 8 wherein the herbicidal salt is a dimethylamine, triethylamine, potassium, or ethanolamine salt of 2,4-D or MCPA.

12. A method as claimed in claim 9 wherein the water-insoluble herbicide is a 1-butoxy-2-propyl, 1-butoxy-2-butyl, 1-(1-methoxy-2-propoxy)-2-propyl, 1-(1-butoxy-2-propoxy)-2-propyl, 1(1-(1-methoxy-2-propoxy)-2-propoxy)-2-propyl, 1-(1-(1-butoxy-2-propoxy)-2-propoxy)-2-propyl, or 2-ethylhexyl ester of fluroxypyr.

13. A method as claimed in claim 9 wherein the herbicidal salt is a dimethylamine, triethylamine, potassium, or ethanolamine salt of 2,4-D or MCPA.

* * * * *